United States Patent [19]

Jackson et al.

[11] Patent Number: 5,371,247

[45] Date of Patent: Dec. 6, 1994

[54] PREPARATION OF SUBSTITUTED ETHENES

[75] Inventors: Arthur Jackson, Washington; Graham Heyes, Durham; James I. Grayson, Western Hill; Paul E. Rowney, Acklam, all of England

[73] Assignee: Fine Organics Limited, London, England

[21] Appl. No.: 730,963

[22] PCT Filed: Apr. 4, 1990

[86] PCT No.: PCT/GB90/00501

§ 371 Date: Jul. 18, 1991

§ 102(e) Date: Jul. 18, 1991

[87] PCT Pub. No.: WO90/12002

PCT Pub. Date: Oct. 18, 1990

[30] Foreign Application Priority Data

Apr. 5, 1989 [GB] United Kingdom ............. 8907700.2

[51] Int. Cl.$^5$ ................... C07D 317/44; C07C 209/00
[52] U.S. Cl. ................................... 549/443; 564/485; 564/340; 546/246

[58] Field of Search ............... 564/485, 340; 549/443; 546/246

*Primary Examiner*—C. Warren Ivy
*Assistant Examiner*—A. A. Owens
*Attorney, Agent, or Firm*—Kane, Dalsimer, Sullivan, Kurucz, Levy, Eisele and Richard

[57] ABSTRACT

A potassium salt useful in the production of certain N-substituted alkyl or arylalkyl thionitroethenamines is produced by the reaction of the dipotassium salt of a 2-nitrodithio aliphatic acid such as 2-nitrodithio acetic acid with branched chain primary alkylamines, secondary alkylamines, arylalkylamines or heterocyclic alkylamines such as dimethylamine, pinacolylamine, benzylamine or piperonylamine, thereby converting one only of the KS-groups to an alkylamine group. The resulting monopotassium salt may be alkylated or arylalkylated to produce an N-substituted alkyl or arylalkyl thionitroethenamine. This compound may be reacted with a suitable amine to produce compounds containing the pharmaceutically active grouping —NHC(=C-HNO$_2$)NHX, wherein X represents an alkyl, arylalkyl or heterocyclic alkyl group.

20 Claims, No Drawings

PREPARATION OF SUBSTITUTED ETHENES

BACKGROUND OF THE INVENTION

1. Field of the Invention

The present invention relates to certain substituted ethenes, specifically certain N-substituted alkyl or arylalkyl thionitroethenamines, derivatives thereof, intermediates in the production thereof and processes for the manufacture of all the aforesaid.

2. Brief Description of the Related Art

In general terms the said family of nitroethenes is known, although certain particular nitroethenes disclosed herein are believed to be novel, and have known uses as intermediates in the manufacture of pharmaceutical compounds such as the histamine $H_2$ antagonists containing the pharmaceutically active end group $-NHC(=CHNO_2)NHX$ wherein X is an organic radical, for example niperotidine which has the formula

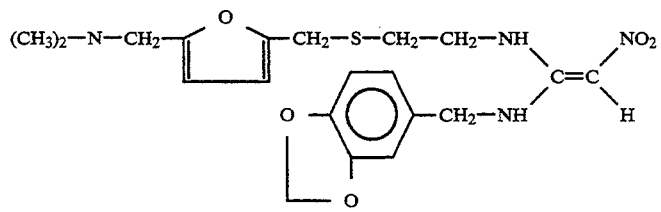

Spanish Patent Specification No. 523448 describes the preparation of N-methyl-1-methylthio-2-nitroethenamine from the dipotassium salt of 2-nitrodithioacetic acid (1-nitro-2,2-bismercapto-ethylene) by a three stage process involving firstly the methylation of one only of the KS-groups by reaction with dimethyl sulphate, secondly the conversion of the resulting $CH_3S$-group into a $CH_3NH-$ group by reaction with methylamine and thirdly, the methylation of the second KS-group by reaction with a further quantity of dimethyl sulphate. This patent is silent as to any possibility for producing other N-substituted thionitroethenamines.

The process described in the Spanish Patent requires careful control at all stages to avoid the production of unwanted reaction products such as the bis(methylthio) derivative and is disadvantageous in requiring a repetition of the dimethyl sulphate reaction due to the toxic nature of that compound.

It is known in the chemical art that, in general, amines do not react with dianions since the lone pair electrons on the amine inhibit reaction with a molecule which is already doubly negatively charged. This inhibition does not apply to dimethyl sulphate. The processing sequence of the Spanish Patent No. 523448 is therefore in accord with current belief in the art.

The present applicant has found, however, that certain amines can be made to react directly with the 2-nitrodithioacetate dianion. This has enabled a highly selective two stage process for the production of aminosubstituted thiosubstituted nitroethenes to be developed.

SUMMARY OF THE INVENTION

The present invention provides a method for the production of a monopotassium salt useful in the production of N-substituted alkyl or arylalkyl thionitroethenamines characterised by reacting an amine selected from branched chain primary alkylamines, secondary alkylamines, arylalkylamines and heterocyclic alkylamines, wherein the alkyl moieties of said arylalkylamines and heterocyclic alkylamines are not straight chain primary amines containing a heteroatom in the chain, with the dipotassium salt of a 2-nitrodithioaliphatic acid.

This process is robust in that it does not require close control at each process step, does not oversubstitute at all during the amination to give the bisaminated derivative and can give an excellent yield.

The monopotassium salt so obtained may be alkylated or arylalkylated to give the required alkyl or arylalkyl thionitroethenamine.

DETAILED DESCRIPTION OF THE INVENTION

In the case of the simplest dipotassium salt, namely dipotassium 2-nitrodithioacetate (also known as dipotassium nitrothiolothionoacetate), and an amine, such as dimethylamine, the sequence of reactions outlined above is as follows:

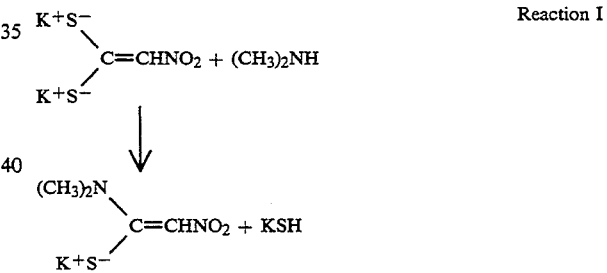

Reaction I

This intermediate may then be converted to N,N-dimethyl-1-methylthio-2-nitroethenamine by reaction with a methylating agent, such as dimethyl sulphate, as follows:

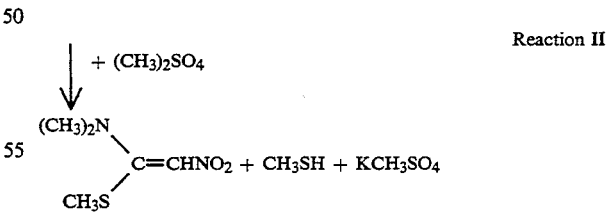

Reaction II

These reactions proceed analogously when using other alkyl, arylalkyl or heterocyclic alkyl amines in Reaction I or other alkylating or arylalkylating agents in Reaction II.

Other amines the use of which is within the scope of the present invention may be selected from other secondary aliphatic amines, substituted or branched chain aliphatic amines, for example pinacolylamine (3-amino-2,2-dimethyl-butane), arylalkylamines, for example benzylamine (aminotoluene); heterocyclic alkylamines, for example piperonylamine (3,4-methylene-dioxybenzylamine or dioxyaminotoluene).

The dipotassium salt of 2-nitrodithioacetic acid required as a starting material may be prepared by the method of E Freund, Chem. Ber. 52, 542 (1919) which produces an ethanol-wet cake. Weights given herein are on a 100% basis, the ethanol being treated as solvent. Analogues of the dipotassium salt of 2-nitrodithioacetic acid, such as those based on butene and propene, can be made by analogous methods.

We prefer to carry out the amination reaction (Reaction I) in a polar solvent, for example, water, methanol, ethanol, isopropanol or dimethyl sulphoxide. On costs and ease of handling, water is the preferred solvent. The reaction concentration (water or other solvent to dipotassium salt of nitrodithioacetic acid) can be 20:1 to 1:1, but is preferably 10:1 to 5:1 by weight.

Any ethanol present in the dipotassium salt of nitrodithioacetic acid as prepared is included as solvent in the above ranges of concentrations and reference to an aqueous solvent includes such minor contents of polar organic solvents. All concentrations quoted herein are in parts by weight unless otherwise stated.

For the amination stage good yields can be obtained using an amine:dipotassium salt of nitrodithioacetic acid molar ratio of 0.8:1 to >2:1 but for the best economics a ratio of 1.1:1 is preferred.

The reaction temperature for the amination reaction can be in the range 0° C. to 100° C. but it is preferably between 20° C. and 60° C. The amination product may be used as a solution as formed or may be recovered.

The alkylation or arylalkylation reaction to convert the thioamide salt to the thio-alkyl derivative (Reaction II) can be carried out in the range 0° C. to 60° C., but it is preferably carried out in the range 10° C. to 40° C. so as to give an acceptable reaction time and avoid side reactions.

Suitable alkylating or arylalkylating agents are alkyl halides or sulphates and the benzyl halides. Particularly convenient agents are dimethyl sulphate, diethyl sulphate, methyl chloride, methyl bromide, methyl iodide and benzyl chloride. Conveniently the alkylation or arylalkylation is effected in the presence of a phase transfer agent such as benzyltrimethylammonium chloride.

During the alkylation or arylalkylation stage, molar ratios of alkylating/arylalkylating agent : dipotassium salt of nitrodithioacetic acid of 1:1 to >4:1 can be used, but optimum yields are obtained using a molar ratio of 2:1 to 2.5:1.

The product nitroethenamine may be recovered by conventional workup procedures such as filtration or, preferably, by extraction of the product directly from the reaction mixture using a suitable organic solvent which is, preferably, a water immiscible chlorinated solvent such as methylene chloride, ethylene dichloride or chlorobenzene. This may be followed by drying, concentrating and recrystallising from a suitable solvent such as propan-2-ol.

The nitroethenamine produced as above described may be further reacted with an amine to produce a compound having the grouping —NC(=CHNO$_2$)NHX where X represents an alkyl arylalkyl or heterocyclicalkyl group. For example, where the dipotassium salt is dipotassium nitrodithioacetate, where the amine used in Reaction I is piperonylamine and where the alkylated or arylalkylated product of Reaction II is then reacted with 2-[5-(N,N-dimethylaminomethyl)-2-furanmethylthio]ethylamine the product is the pharmaceutically active compound niperotidine. Other active materials may be produced using different variants on Reaction I and II, for example where the same dipotassium salt is used and wherein the amine used in Reaction I is pinacolylamine and where the product of reaction II is reacted with a range of aryl or heteroaryl amines such as 4-aminopyridine in particular, a range of compounds having hypotensive properties may be produced.

It is understood that it is also within the scope of the present invention to conduct the analogous process to that set out above for the production of compounds containing the said grouping —NC(=CHNO)NHX wherein the amination Of Reaction I and the further amination are reversed in position. This concept of an analogous process extends over the full range of amines described above as appropriate to Reaction I and to the further amination.

In order that the present invention may more readily be understood, certain preparations in accordance therewith will now be described in detail.

EXAMPLE 1

N Benzyl-1-methylthio-2-nitroethenamine

Dipotassium nitrodithioacetate (64.7 g) dissolved in 280 ml of water was heated to 40° C. and benzylamine (48.7 g) was then added over 1 hour. After heating to 60° C. and maintaining this temperature for 4 hours the reaction mixture was cooled to ambient temperatures and stirred overnight. Benzyltrimethylammonium chloride (4 g), was then charged followed by dimethyl sulphate (106 g) over one hour. After stirring for a further 6 hours, the precipitated solid was filtered off and recrystallised from 2-propanol to give 31 g (46%) of the title compound (m.p. 112° C.).

EXAMPLE 2

N,N Dimethyl-1-methylthio-2-nitroethenamine

To a solution of dipotassium nitrodithioacetate (118 g) dissolved in water (630 ml), dimethylamine (1.1 equivalents) was added as a 40% w/w solution in water. After stirring for 6 hours at 20°-25° C., benzyltrimethylammonium chloride (7 g) was charged followed by dimethyl sulphate (175 g) over one hour. After stirring overnight, the reaction mixture was extracted three times with 100 ml aliquots of dichloromethane. After drying over MgSO$_4$, the combined organic phases were concentrated to a red oil which was chromatographed on a silica gel column, using ethyl acetate as eluant to give, after recrystallisation from isopropanol, 36 g (40%) of the title compound, m.p. 60° C.

EXAMPLE 3

N-(1-methyl-2,2-dimethylpropyl)-1-methylthio-2-nitroetheneamine

To an aqueous solution of dipotassium nitrodithioacetate (300 g 15% by weight) was added pinacolylamine (32 g) over 1 hour. After heating to 60° C. and maintaining this temperature for 4 hours, the reaction mixture was cooled to ambient temperatures and stirred overnight. Benzyltrimethylammonium chloride (3 g), was then charged, followed by dimethyl sulphate (66 g) over one hour. After stirring overnight, the reaction mixture was extracted three times with 50ml aliquots of dichloromethane. After drying over MgSO$_4$, the combined organic phases were concentrated and the residue recrystallised from 2-propanol to give 13 g (33%) of the title compound (m.p. 69° C.) which is believed to be novel.

EXAMPLE 4

N-(3,4-methylenedioxymethyl) 1-Methylthio-2-nitroethenamine

A 15% w/w solution of dipotassium nitrodithioacetate (303 g), piperonylamine (45.3 g) and dichloroethane was heated to reflux for one hour. The organic phase was separated off and to the aqueous phase at 20° C.,benzyltrimethylammonium chloride (1 g) was added followed by dimethyl sulphate (75 g) which was added over 1 hour. The reaction mixture was stirred overnight and the precipitated title compound recrystallised from acetone to give 24 g (42%) (m.p. 126° C.).

We claim:

1. A method for the production of a mono-potassium salt useful as an intermediate in the production of N-substituted alkyl- or arylalkyl-thionitroethenamines, which comprises; reacting an amine selected from branched chain primary alkylamines, secondary alkylamines, arylalkylamines and heterocyclic alkylamines, wherein the alkyl moieties of said arylalkylamines and heterocyclic alkylamines are not straight chain primary amines containing a heteroatom in the chain, with the dipotassium salt of a 2-nitrodithioacetic.

2. A method as claimed in claim 1, characterised in that the amine is selected from dimethylamine, pinacolylamine, benzylamine and piperonylamine.

3. A method as claimed in claim 1, characterised in that the method is carried out in an aqueous or organic polar solvent medium at a reaction concentration of solvent medium to dipotassium salt of 20:1 to 1:1 by weight, a molar ratio of amine to dipotassium salt of 0.8:1 to 2:1 a reaction temperature of 0° C. to 100° C. for a duration such that the reaction has substantially completed.

4. A method for the production of an N-substituted S-substituted thionitroethenamine characterised in that the method comprises preparing a mono-potassium salt by a method according to claim 1 alkylating or arylalkylating the mono-potassium salt and recovering the product.

5. A method as claimed in claim 4, characterised in that the alkylation or arylalkylation is conducted by reacting the mono-potassium salt with an agent selected from dimethyl sulphate, diethyl sulphate, methyl chloride, methyl bromide, methyl iodide and benzyl chloride.

6. A method as claimed in claim 5, characterised in that the alkylation or arylalkylation is conducted in the presence of a phase transfer agent.

7. A method as claimed in claim 4, characterised in that the method comprises introducing the alkylating or arylalkylating agent into the mono-potassium salt/solvent mixture produced according to claim 1.

8. A method as claimed in claim 4, characterised in that the molar ratio of alkylating or arylalkylating agent to the dipotassium salt is at least 1:1, the reaction temperature is from 0° C. to 60° C. and the reaction duration is such that the reaction has substantially completed.

9. A method as claimed in claim 4, characterised in that the product nitroethenamine is recovered by filtration.

10. A method as claimed in claim 4 characterised in that the product nitroethenamine is recovered by solvent extraction.

11. A method as claimed in claim 7 and wherein the mono-potassium salt is produced in aqueous medium, characterised in that the product ethenamine is recovered by extraction in a water immiscible chlorinated organic solvent.

12. A method as claimed in claim 7 wherein the second amine is 2-[N,N-dimethylaminomethyl)-2-furanmethylthio]ethylamine.

13. A method as claimed in claim 7 wherein the second amine is piperanyl-amine and the product is the pharmaceutically active niperotidine.

14. A method for the production of a compound containing the grouping —NC(=CHNO$_2$)NHX wherein X represents an alkyl, arylalkyl or heterocyclic alkyl group which comprises; reacting the dipotassium salt of 2-nitrodithioacetic acid with a first amine selected the group consisting of branched chain primary alkylamines, secondary alkylamines, arylalkylamines and heterocyclicalkyl amines, wherein the alkyl moieties of said arylalkylamines and heterocyclic amines are not straight chain primary amines containing a heteroatom in the chain, whereby there is formed the mono-potassium salt of the 2-nitrodithioacetic acid; alkylating or arylalkylating the mono-potassium salt; and reacting the alkylated or arylalkylated salt with 2-[5-(N,N-dimethylaminomethyl)-2-furanmethylthio]ethylamine.

15. A method as claimed in claim 14 wherein the first amine is piperonylamine and wherein the product is the pharmaceutically active compound niperotidine.

16. A method for the production of a compound containing the grouping —NC(=CHNO$_2$)NHX wherein X represents an alkyl, arylalkyl or heterocyclic alkyl group which comprises; reacting the dipotassium salt of 2-nitrodithioacetic acid with 2-[5-N,N-dimethylaminomethyl)-2-furanmethylethio]ethylamine whereby there is formed the mono-potassium salt of the 2-nitrodithioacetic acid; alkylating or arylalkylating the mono-potassium salt; and reacting the alkylated or arylalkylated salt with a second amine.

17. A method as claimed in claim 16 wherein the second amine is piperanylamine and the product is pharmaceutically active niperotidine.

18. A method for the production of a compound containing the grouping —NC(=CHNO$_2$)NHX wherein X represents an alkyl, arylalkyl or heterocyclic alkyl group, which comprises:
  reacting the dipotassium salt of 2-nitrodithioacetic acid with 2-[5-N,N-dimethylaminomethyl)-2-furanmethylethio]ethylamine whereby there is formed the mono-potassium salt of the 2-nitrodithioacetic acid;
  alkylating or arylalkylating the mono-potassium salt; and
  reacting the alkylated or arylalkylated salt with a second amine selected from the group consisting of branched chain alkylamines, arylalkylamines and heterocyclioalkyl amines, wherein the alkyl moieties of said arylalkylamines and heterocyclic amines are not straight chain primary amines containing a heteroatom in the chain.

19. A method for the production of a pharmaceutically active niperotidine, which comprises:
  reacting the dipotassium salt of 2-nitrodithioacetic acid with piperoanylamine, whereby there is formed the mono-potassium salt of the 2-nitrodithioacetic acid;

alkylating or arylalkylating the mono-potassium salt; and reacting the alkylated or arylalkylated salt with a second amine selected from the group consisting of branched chain alkylamines, arylalkylamines and heterocycloalkyl amines, wherein the alkyl moieties of said arylalkylamines and heterocyclic amines are not straight chain primary amines containing a heteroatom in the chain.

20. N-(1-methyl-2,2-dimethylpropyl)-1-methylthio-2-nitroethenamine.

* * * * *